(12) United States Patent
Fox et al.

(10) Patent No.: US 11,376,406 B2
(45) Date of Patent: Jul. 5, 2022

(54) APPLICATOR DEVICE FOR APPLYING SPECIFIC AMOUNTS OF TOPICAL SUBSTANCES ONTO THE SKIN

(71) Applicant: BACKLICATOR LLC, New York, NY (US)

(72) Inventors: Shelley Fox, New York, NY (US); Raphael Cices, New York, NY (US)

(73) Assignee: BACKLICATOR LLC, New York, NY (US)

( * ) Notice: Subject to any disclaimer, the term of this patent is extended or adjusted under 35 U.S.C. 154(b) by 171 days.

(21) Appl. No.: 16/655,975

(22) Filed: Oct. 17, 2019

(65) Prior Publication Data

US 2020/0121899 A1    Apr. 23, 2020

Related U.S. Application Data

(60) Provisional application No. 62/747,770, filed on Oct. 19, 2018.

(51) Int. Cl.
*A61M 35/00*    (2006.01)

(52) U.S. Cl.
CPC ..... *A61M 35/003* (2013.01); *A61M 2209/082* (2013.01)

(58) Field of Classification Search
CPC ...... A61M 35/003–006; A61M 5/2422; A61M 5/20; A46B 11/0055; B05C 17/005
See application file for complete search history.

(56) References Cited

U.S. PATENT DOCUMENTS

| 5,875,920 A | 3/1999 | Parent |
| 6,238,118 B1 | 5/2001 | Tyron |
| 6,964,536 B1 | 11/2005 | Alhateeb |

(Continued)

FOREIGN PATENT DOCUMENTS

CN    205075029 U    3/2016

OTHER PUBLICATIONS

PCT International Search Report of International Application No. PCT/US19/56739, dated Jan. 6, 2020.

(Continued)

*Primary Examiner* — Tatyana Zalukaeva
*Assistant Examiner* — Meagan Ngo
(74) *Attorney, Agent, or Firm* — J.A. Lindeman & Co. PLLC (57) ABSTRACT

An applicator device allows for independent application of topical substances onto patients' skin, allowing self-application to difficult-to-reach areas. The applicator device includes a handle, an articulating segment, and an applicator head. The handle extends to a rotating joint between the handle and the articulating segment. A user activates the handle that operates to deliver the topical substance from an incorporation portion of the articulating segment to the applicator head and to the patient. The device meters the dispensed doses. The device can use disposable foam applicator pads and comes in a sleek, modern, ergonomic design. The device articulates and folds and rotates to provide easy access to previously hard-to-reach patient areas. The device can be easily stored, cleaned, and disinfected. The device prevents wasting of substances and solves the problem of overuse of topical medications, which can lead to adverse side effects.

8 Claims, 10 Drawing Sheets

(56) References Cited

U.S. PATENT DOCUMENTS

| | | | |
|---|---|---|---|
| 7,435,029 B1 | 10/2008 | Marini | |
| 8,382,727 B1* | 2/2013 | Martin | A45D 34/041 |
| | | | 604/289 |
| 2003/0178446 A1 | 9/2003 | Osgood | |
| 2006/0075592 A1* | 4/2006 | Sommers | A45D 34/04 |
| | | | 15/244.1 |
| 2008/0114315 A1* | 5/2008 | Voegele | A61M 35/003 |
| | | | 604/311 |
| 2009/0093743 A1* | 4/2009 | Corzine | A61H 7/003 |
| | | | 601/136 |
| 2011/0137268 A1* | 6/2011 | Thomason | B05B 7/1209 |
| | | | 604/291 |
| 2012/0259237 A1* | 10/2012 | Axelrod | A61M 5/1452 |
| | | | 600/506 |
| 2017/0113029 A1* | 4/2017 | Hernandez | A61M 35/003 |
| 2017/0164713 A1* | 6/2017 | Davia | A61B 17/54 |

OTHER PUBLICATIONS

PCT International Preliminary Report on Patentability of International Application No. PCT/US19/56739, dated Jan. 6, 2020.

* cited by examiner

FIG. 1A-1C - FOLDING/UNFOLDING THE DEVICE

FIG. 1D - 1F
Folding and Unfolding the Device

FIG. 4A-C – ADVANCING MECHANISM: CABLE, RETRACTED

FIG. 7 - EXPLODED VIEW

FIG. 8
Applicator Heads

APPLICATOR DEVICE FOR APPLYING SPECIFIC AMOUNTS OF TOPICAL SUBSTANCES ONTO THE SKIN

TECHNICAL FIELD

The invention relates to applicators for dispensing and applying a substance to various body parts. More specifically, the invention relates to applicator devices that apply a metered amount of topical substances, including medicine, onto the skin of a person or patient.

BACKGROUND

Many people experience trouble while attempting to apply topical treatments to body parts that are difficult to access. Specifically, patients with dermatologic conditions on their backs or who have undergone surgical procedures on their backs struggle to apply the appropriate amounts of topical therapies such as lotions, creams, gels, and ointments to the affected areas. Furthermore, patients who are obese, who have physical disabilities, are wheelchair bound, or who live alone may have even greater difficulties applying topical substances onto their backs or other body parts that may be difficult to reach. Sometimes a dermatologist will not prescribe the best topical treatment available, and will instead prescribe an oral medication, because patients cannot adequately apply topical medications to their backs. Oral medications have a plethora of side effects compared to topical treatments, and patients need to try the best efficacious topical treatments first.

Lotion applicators exist to help dispense topical treatments onto the body. However, none of the current devices allow for people to reach certain areas of the body while also ensuring patients apply only a specific amount of the topical substance. The importance of applying specific amounts ensures that secondary side effects do not occur from overuse of a topical agent or even in rare cases, systemic toxicity due to overuse of topical medications. In the same regard, applying generous amounts of a cream may be necessary for larger surface areas of the body affected by dermatologic conditions such as acne, rashes, or superficial skin infections. Large amounts of cream may be necessary when applying sunscreen to the body to ensure coverage of the entire back in its entirety to prevent subsequent sunburns that may increase the risk of skin cancer.

In addition, dermatology patients also face the struggle of how to apply healing creams to rashes and wounds on their backs after having skin biopsies and surgeries. It is crucial that patients be able to apply these creams on their backs to prevent complications, such as infection, after procedures. Application of creams also helps to prevent disfiguring scars, but if a patient cannot reach the affected area, they are at increased risk for complications. Back pain is also a very common condition and a lotion applicator may assist in applying topical analgesics to affected areas of the back.

SUMMARY

The invention solves the major problem of people who cannot adequately apply topical substances. The invention allows patients to reach hard-to-access areas and provides a metered dose of medication to ensure that patients do not put on too much medication or too little.

The invention includes an applicator device with a handle, a main body, a metering device, and an applicator member. The handle includes a trigger or a button to initiate dispensing of a substance, such as a topical ointment, medicine, lotion, gel, and the like. A cable triggers a slider within an applicator arm, which mobilizes a plunger of a syringe (cartridge), subsequently pushing a topical substance through an orifice in the applicator member, which delivers the (topical) substance to a desired area of the person.

This invention solves the problem of applying specific amounts of topical substances to difficult-to-reach body regions. This applicator device invention applies specific metered doses of a variety of solutions, lotions, creams, ointments, compounds, and gels to any body part, especially those areas that are difficult for a patient to reach without assistance. Patients who do not have a caregiver that is able to assist them in applying topical substances to their various body parts can benefit from an applicator device of the invention as it can dispense exact quantities of substances to the exact location needed.

This avoids overuse of lotions and creams and prevents waste while ensuring that the proper dose is delivered to the affected area on the patient's body. Additionally, the invention allows for application of topical substances to contagious skin infections while never having to physically touch one's own skin (or another's skin) and thus prevents the spread of disease.

An applicator device of the invention provides for self-administration of a topical substance to a difficult-to-reach location of a patient. An applicator device includes a handle, an articulating segment, and an applicator head. The handle includes a proximal end extending along a first arm to a distal end, an actuation path of the handle extending from the proximal end to the distal end, and a rotating joint at the distal end. The articulating segment includes a joint end extending along a second arm to an applicator end, and an incorporation portion of the second arm between the joint end and the applicator end. The incorporation portion is configured to accept the topical substance to be administered to the patient. The articulating segment is operably connected to the handle via the rotating joint at the joint end. The applicator head for administering the topical substance to the patient is in fluid communication with the incorporation portion of the articulating segment to administer the topical substance to the patient.

An applicator device of the invention can also include an actuator positioned in the handle and configured to initiate administration of the topical substance to the patient when activated. An applicator device of the invention can also include an actuator including a cable extending from the handle through the rotating joint to a slider in the articulating segment, and the actuator can also activate the cable and displaces the cable a pre-determined distance each time it is activated to mobilize a driver that propels the topical substance through the incorporation portion along a flow path to an orifice in the applicator head, to administer a metered dose of the topical substance to the patient.

An applicator device of the invention can also include an incorporation portion, which accepts a cartridge holding a topical substance to be administered to the patient. A device of the invention can also include an actuator that activates the cable and displaces the cable a pre-determined distance each time it is activated. The activation mobilizes a driver to propel the topical substance from the cartridge through the incorporation portion along a flow path to the orifice in the applicator head to administer a metered dose of the topical substance to the patient. An applicator device of the invention can also include a cartridge, such as a syringe. A driver can also include a syringe plunger that forces the topical substance from the syringe to the orifice in the applicator head to administer the metered dose of the topical substance to the patient.

An applicator device of the invention can also activate the actuator to move a shuttle slider assembly that moves along pins and advances the cable via an advancing cam. The advancing cam pushes a roller follower upward causing a pawl assembly to rotate about a pawl axis spring resulting in longitudinal motion of a ratcheting pawl in the opposite direction of the cable. The ratcheting pawl engaging teeth on the syringe plunger mobilize the syringe plunger to force the topical substance to the orifice in the actuator head to administer the metered dose of the topical substance to the patient. An applicator device of the invention can also include a metered dose determined by at least one of a number of activations of the actuator, tooth spacing on the syringe plunger, and internal cross-sectional area of the syringe.

An applicator device of the invention can also include a rotating joint that includes two pulleys through which the cable extends coaxially through the rotating joint from the handle to the articulating member. Further, an applicator device of the invention can also include a rotating joint, which includes a joint unlocking button configured to hold the handle and the articulating segment in a predetermined closed position relative to each other and to position the handle and the articulating segment in an extended configuration when engaged. Additionally, an applicator device of the invention can also include a joint unlocking button which includes a joint locking wheel with a notch to engage the rotating joint to hold the handle and the articulating segment in a predetermined extended configuration when engaged. An applicator device of the invention can also include an extendible handle and/or articulating segment to elongate the applicator device to up to an additional eight (8) inches in overall length, as measured from the proximal end of the handle to the applicator head on the articulating segment.

An example applicator device of the invention includes a handle, an articulating segment, an applicator head, and a cartridge that includes a topical substance. The handle includes a proximal end extending along a first arm to a distal end, an actuation path of the handle extending from the proximal end to the distal end, and a rotating joint at the distal end. The articulating segment includes a joint end extending along a second arm to an applicator end, and an incorporation portion of the articulating segment between the joint end and the applicator end. The incorporation portion can be configured to accept a cartridge holding the topical substance to be administered to the patient. The articulating segment is operably connected to the handle via the rotating joint at the joint end. The applicator head for administering the topical substance to the patient is in fluid communication with the cartridge to administer the topical substance to the patient. The cartridge includes the topical substance to be administered to the patient. An actuator propels the topical substance from the cartridge through the incorporation portion of the articulating segment along a flow path to an orifice in the applicator head to administer a metered dose of the topical substance to the patient.

An applicator device of the invention can also include an actuator positioned in the handle and configured to initiate administration of the topical substance to the patient when activated. An actuator can include a cable extending from the handle through the rotating joint to a slider in the articulating segment. The actuator activates the cable and displaces the cable a pre-determined distance each time it is activated. The activation mobilizes a driver of the cartridge that propels the topical substance through the incorporation portion along a flow path to the orifice in the applicator head to administer the metered dose of the topical substance to the patient.

An applicator device of the invention can also include a cartridge that is a syringe. Further, a driver can also include a syringe plunger that forces the topical substance from the syringe to the orifice in the applicator head to administer the metered dose of the topical substance to the patient. An actuator can move a shuttle slider assembly along pins and advance the cable via an advancing cam. The advancing cam pushes a roller follower upward to cause a pawl assembly to rotate about a pawl axis spring resulting in longitudinal motion of a ratcheting pawl in the opposite direction of the cable. The ratcheting pawl engages teeth on the syringe plunger to mobilize the syringe plunger to force the topical substance to the orifice in the actuator head to administer the metered dose of the topical substance to the patient. An applicator device of the invention can also include a metered dose determined by a number of activations of the actuator, tooth spacing on the syringe plunger, and/or internal cross-sectional area of the syringe.

A storage container for use with an applicator device of the invention can include a containment portion, a driver, and an exit opening. The containment portion holds the topical substance to be administered to the patient. The driver is mobilized by an actuator of the applicator device and forces the topical substance from the containment portion. The exit opening directs a flow path of the forced topical substance from the containment portion to an orifice of the applicator device to administer a metered dose of the topical substance to the patient.

A storage container of the invention can also include a driver, which includes teeth or indentations to ratchet against a pawl of the actuator. A storage container of the invention can be a syringe, where the exit opening is a curved tubing extending from the containment portion of the syringe. Likewise, the driver can be a syringe plunger that forces the topical substance from the syringe to the orifice in the applicator device to administer the metered dose of the topical substance to the patient.

DETAILED DESCRIPTION

Figure 1A:
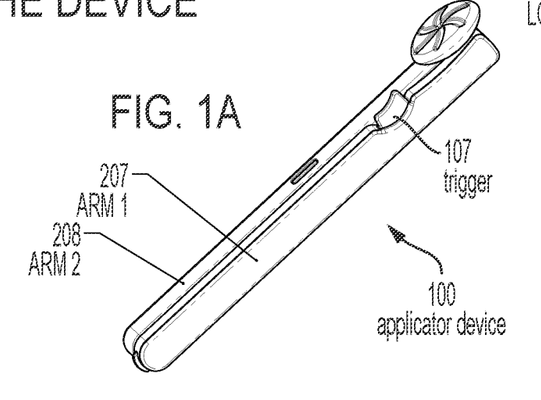
FIG. 1A shows an example applicator device of the invention in a folded configuration.
Figure 1B:
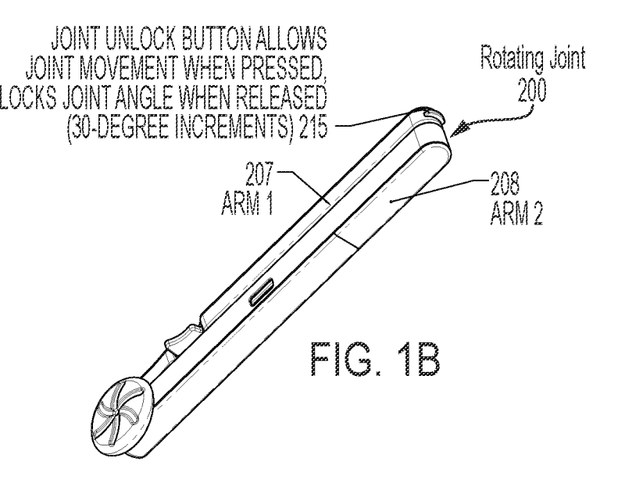
FIG. 1B shows an example applicator device of the invention in a folded configuration.
Figure 1C:
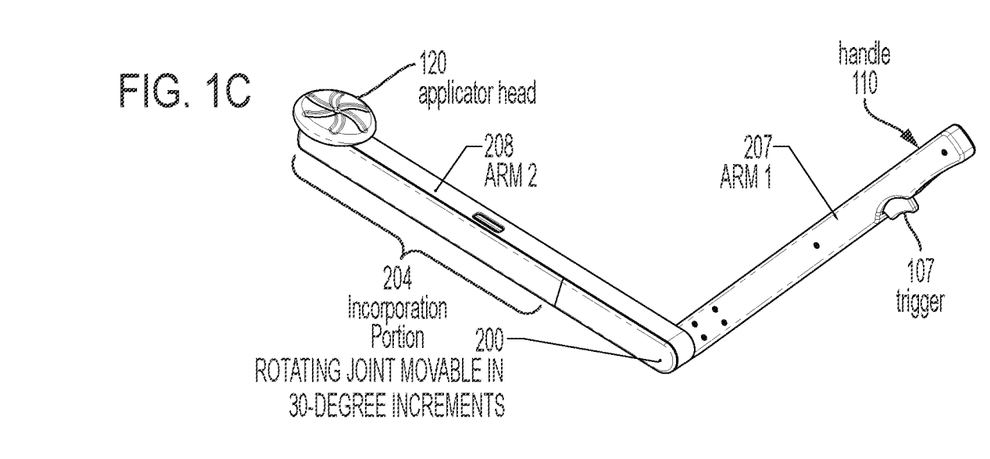
FIG. 1C shows an example applicator device in a partially-extended (unfolded) configuration and reveals the housing of the syringe within the $2^{nd}$ arm.
Figures 1D, 1E, 1F:
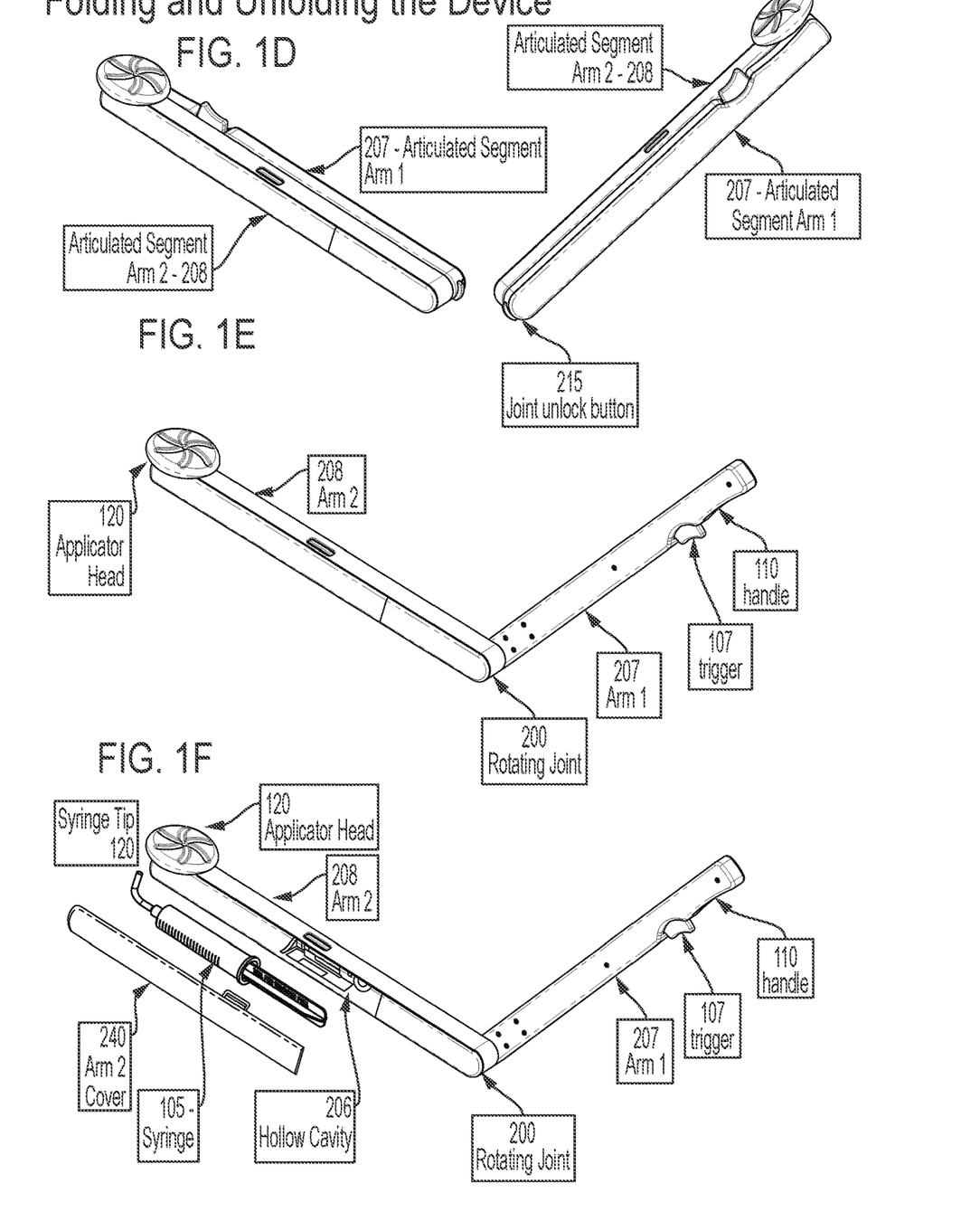
FIG. 1D shows an example applicator device of the invention in a folded configuration.
FIG. 1E shows an example applicator device in a partially-extended (unfolded) configuration and reveals the housing of the syringe within the $2^{nd}$ arm.
FIG. 1F shows an example applicator device in a partially-extended (unfolded) configuration and reveals the housing of the syringe within the $2^{nd}$ arm.

FIGS. 1A-1C show an applicator device 100 in accordance with the invention. As shown further in FIGS. 2A-2B, the configuration and manufacture of the applicator device 100 allows a user to reach all areas of the body on which to apply medicine and other topical substances (e.g., lotion, ointment, and other substances applied directly to the body). The applicator device 100 includes two articulated segments, including Arm 1 (reference numeral 207) and Arm 2 (reference numeral 208), along with an easy-grip (i.e., ergonomically shaped and/or with a grippy texture/material properties) handle 110 as shown in FIG. 1C. For example, the grip of Arm 2 (208) may be made of a rubber material. Further, the handle 110 may be made of plastic, stainless steel, and/or other material or combination of materials that is inflexible. The trigger 107, as shown in FIGS. 1A-1F, is a thumb-trigger on the thumb side of the handle 110 grip. However, in other embodiments, the trigger 107 may be located on the finger side of the handle 110, that is the area on the opposite side of trigger 107 in FIG. 1A-F, for activation by another finger, e.g., index-finger activation.

Figure 6A:
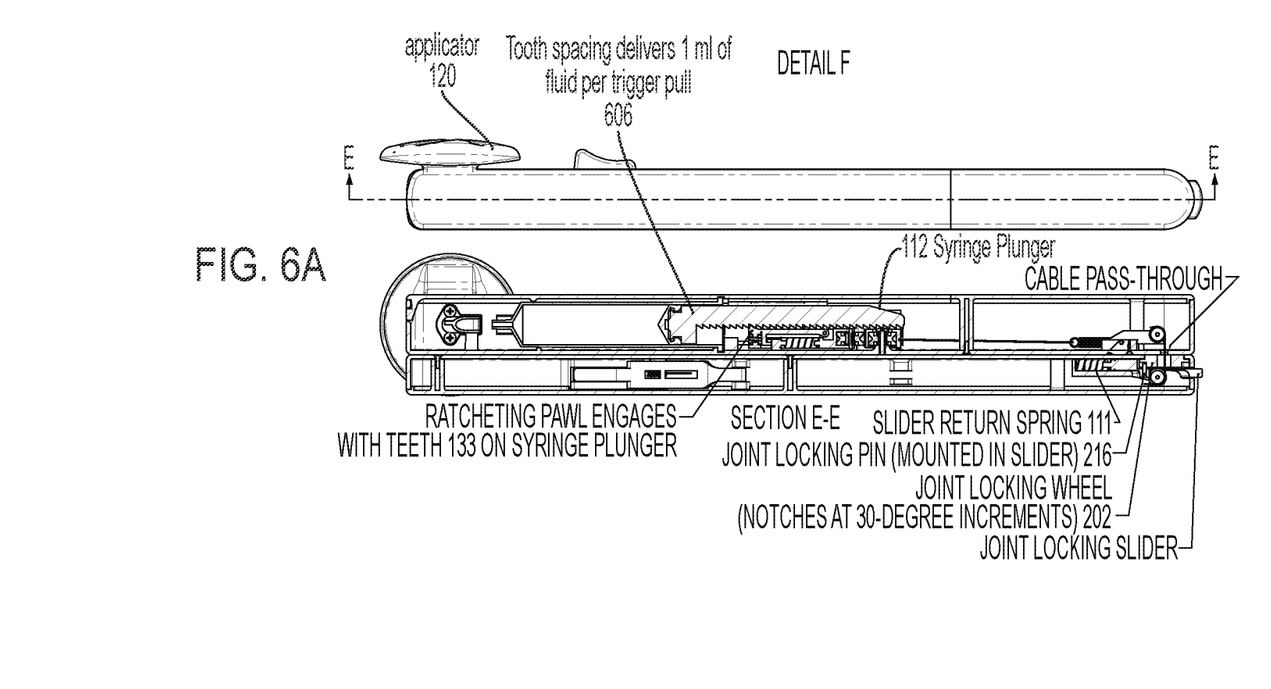
FIG. 6A shows a closed side view of an example applicator device, and bottom-view of internal mechanisms of an example applicator device including a shuttle, locking joint, and syringe cartridge mount that provides for metered dosing.
Figure 7:
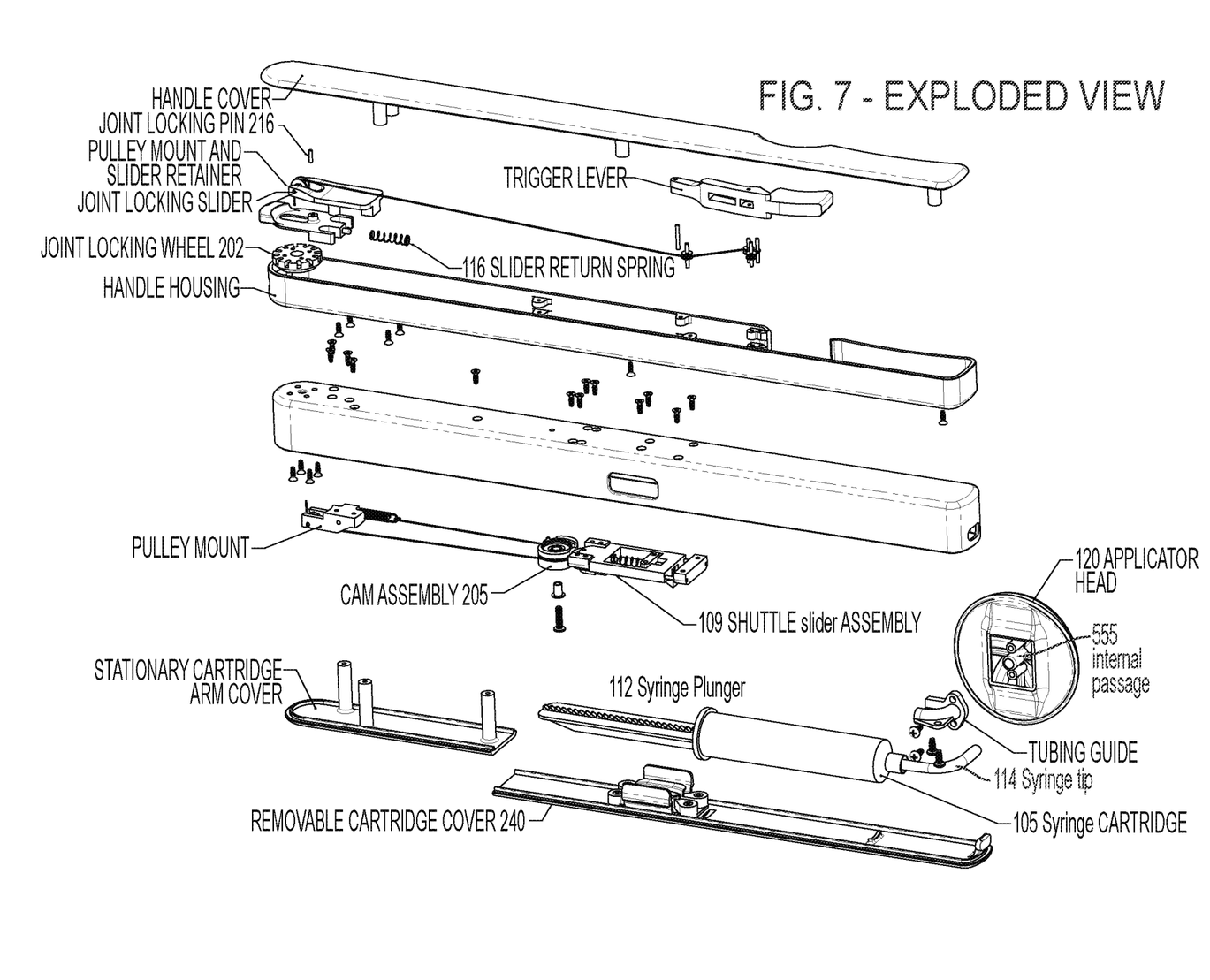
FIG. 7 illustrates an exploded perspective-view of external and internal components of an example applicator device.

As shown in FIGS. 1C, 1F, and 3A-C, the applicator device 100 receives a syringe cartridge 105, or other pre-filled container (holding a topical substance), in an incorporation portion 204 of Arm 2 (208). In particular, the syringe cartridge 105 is placed in the cavity 206 of the incorporation portion 204. The incorporation portion 204 includes a long hollow cavity 206 in Arm 2 (208) of the applicator device 100. As shown in FIG. 1B and throughout the FIGS., the end of Arm 1 (207) is attached to Arm 2 (208) by a rotating joint 200. In other embodiments, the incorporation portion attaches the syringe cartridge to an outer portion of the Arm 2 (208). As shown in FIG. 1B, the rotating joint 200 is activated by pushing the joint unlocking button 215, and the applicator device 100 can be extended or folded using this button 215 in predetermined increments, such as 30 degrees, for example. The unlocking button 215 is held in place with an internal joint locking pin 216 (shown in detail in FIG. 6A and FIG. 7) which keeps the arm in its desired place until the unlocking button 215 is pressed again. FIGS. 6A and 7 detail the mechanisms that aid in unlocking and locking the rotating joint 200 including the joint locking wheel 202 that has notches at 30-degree increments. The arms 207 and 208 can extend up to 180 degrees via the rotating joint 200, and in this fashion, the applicator device 100 can be fully extended to reach a maximum length. The arms 207 and 208 can also fold flush against one another via the rotating joint 200 to be in a fully closed position for easy storage. When the applicator device 100 is in a closed position, the maximum length of the applicator device 100 is between 10 and 20 inches, e.g., 15 inches to provide enough length for reaching all difficult-to-reach locations. When the applicator device 100 is in a fully extended/open configuration, the applicator device 100 is between 20 and 40 inches long, e.g., 34 inches when fully extended to reach difficult-to-reach locations on most patients of different sizes. In some embodiments, the applicator device 100 is different lengths for adults and children, e.g., 34 inches when fully extended for adults and 16 inches when fully extended for children. The applicator device 100 may be configured to meet airline and/or transportation security administration (TSA) guidelines.

In the FIGS, a rotating joint 200 is shown between Arm 1 (207) and Arm 2 (208). The rotating joint 200 can be used to collapse and store the applicator device 100. The applicator device 100 is easily collapsible and may include more than two arms with corresponding rotating joints. The applicator device may collapse and fold at both the handle end and joint end. At either end of the applicator device 100, that is, at Arm 1 (207) and/or at Arm 2 (208), the articulating arms can be extendable and can elongate the applicator device 100 to reach an additional six to eight inches, for example, in order to apply substances to body regions that have been previously difficult to reach. Several different articulating arms of various lengths and shapes provide a flexible geometry of the applicator device 100 as patients of all shapes and sizes can benefit from the applicator device 100.

Several different handles 110 of various lengths and shapes provide a flexible geometry of the applicator device 100 to accommodate patients of all shapes and sizes. The handles 110 may include a grip portion that is between three and five inches long to accommodate different hand shapes/ sizes. For example, handle 110 can extend (for example, an additional two inches to four inches) to elongate the applicator device 100 to reach various body parts. Handle 110 can also bend and collapse for easy storage. As outlined above, the joint 200 can be rotatable to allow the handle-arm junctions to move from a closed configuration (see FIG. 1A, for example) through approximately 90 degrees (as shown in FIG. 1C, for example) to a larger angle, such as 120 degrees, as shown in numerous figures for example, or to a smaller angle, such as 60 degrees. Further, the handle 110 may include an elbow attachment or other hinge joint which can further rotated and/or locked to provide a larger bend radius of the articulating arm(s) when rubbing medications onto the skin. The elbow attachment may be similar to rotating joint 200 which allows locking at different degrees of rotation.

Figure 4A:
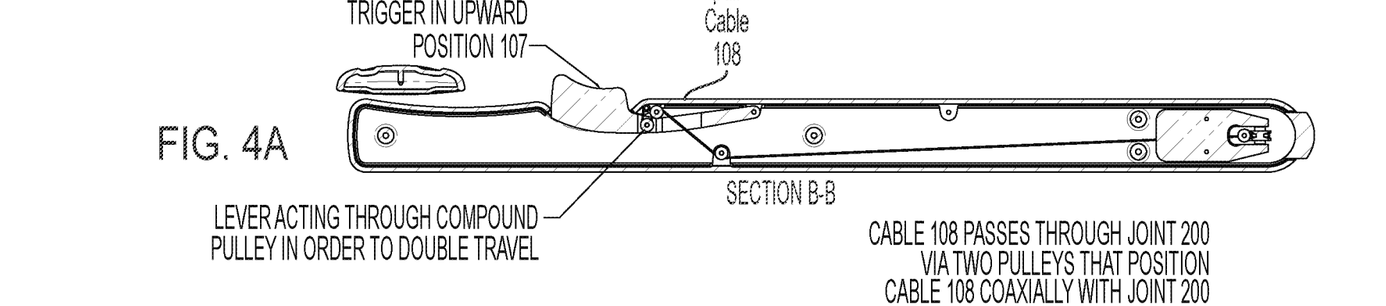
FIG. 4A illustrates a side-view along the B-B cross-sectional line of FIG. 4B, of internal features of an example applicator device including an advancing mechanism including a cable passing through a joint via two pulleys which provide a metered dose of a topical substance.
Figure 4B:
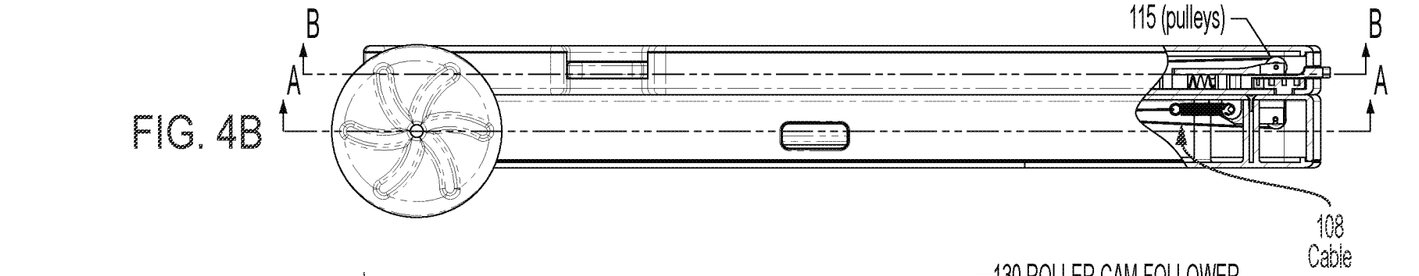
FIG. 4B illustrates a top-view of internal features of an example applicator device including an advancing mechanism including a cable passing through a joint via two pulleys which provide a metered dose of a topical substance.
Figure 4C:
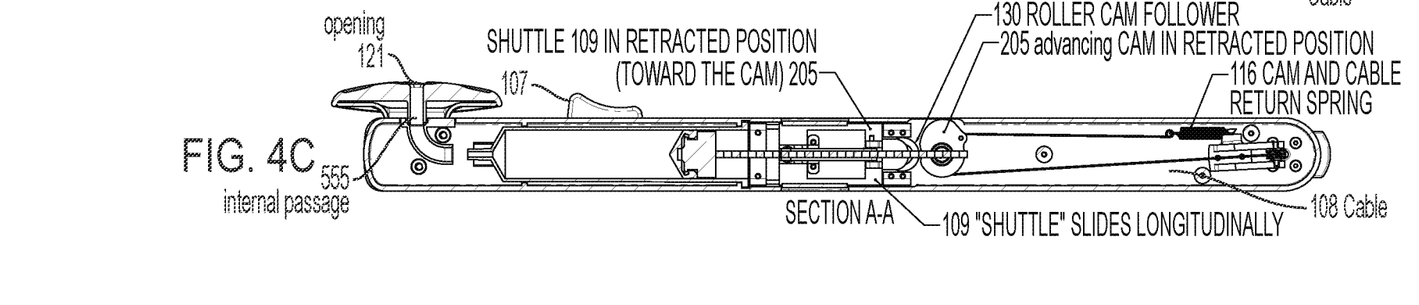
FIG. 4C illustrates a side-view along the A-A cross-sectional line of FIG. 4B, of internal features of an example applicator device including an advancing mechanism including a cable passing through a joint via two pulleys which provide a metered dose of a topical substance.
Figure 5A:
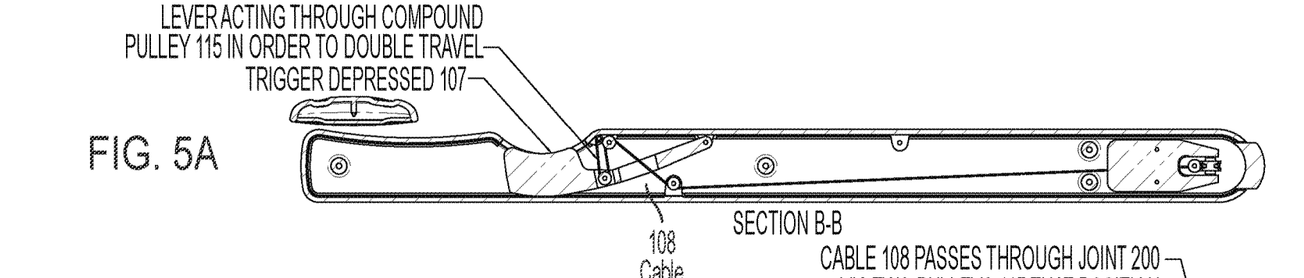
FIG. 5A shows a side-view along the B-B cross-sectional line of FIG. 5B, of internal features of an example applicator device when the trigger mechanism is depressed, and the cables are activated.
Figure 5B:
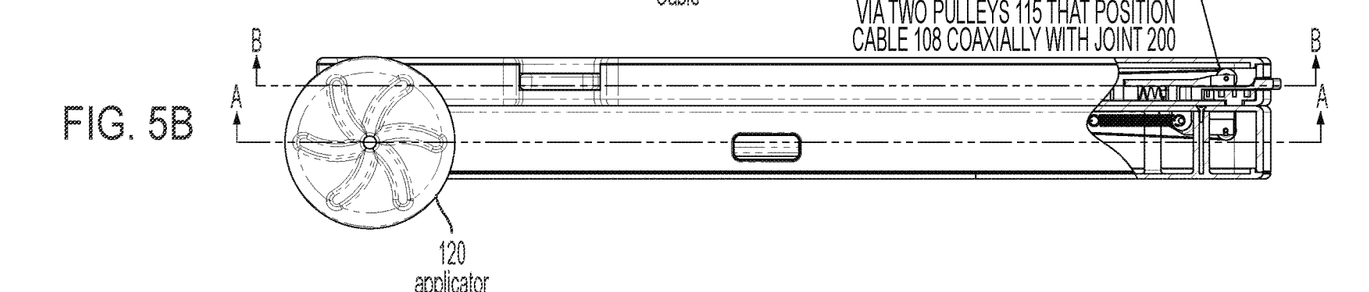
FIG. 5B shows a top-view of internal features of an example applicator device when the trigger mechanism is depressed, and the cables are activated.
Figure 5C:
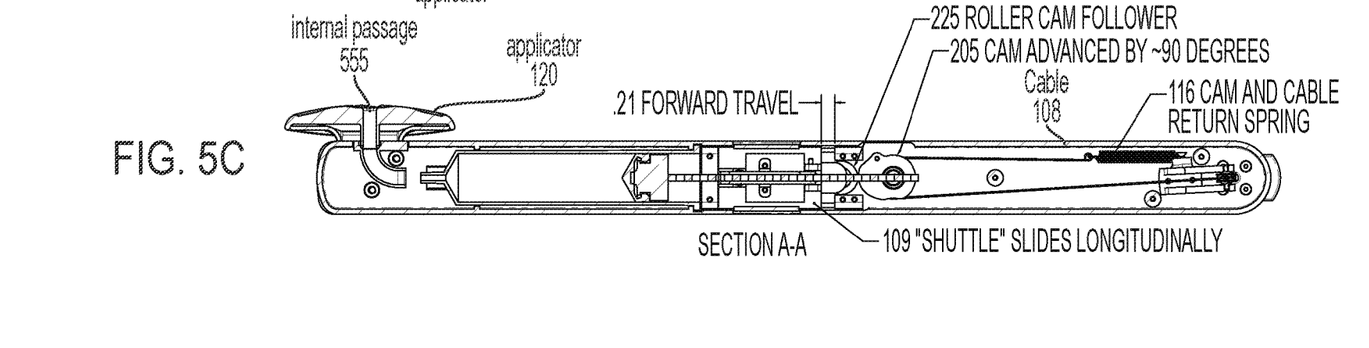
FIG. 5C shows a side-view along the A-A cross-sectional line of FIG. 5B, an example applicator device when the trigger mechanism is depressed, and the cables are activated.

As shown in the FIGS., handle 110 includes a trigger 107 that initiates the flow of medicine (or other topical substance) from syringe 105 (cartridge) using pull cable 108. As shown, the pull cable 108 extends from the Arm 1 (207), through the articulated (rotating) joint 200 and through Arm 2 (208) as shown in FIGS. 5A-5C. As shown in FIG. 4, the cable 108 passes through the joint 200 via two pulleys 115 that position the cable 108 coaxially with the articulated (rotating) joint 200. When trigger 107 is pulled, the trigger 107 activates the pull cable 108, and the cable 108 is displaced a predetermined distance, such as 0.25 inches as shown in one example embodiment in the FIGS. The size of the cable 108, the size of the slider shuttle assembly 109, the size of the opening in the syringe tip 114, the size of the openings 121 in the applicator head 120 (shown in FIG. 8), and the number of times the trigger 107 is activated, can control the amount of topical substance dispensed. Each activation of the trigger 107 equates to the release of a specific amount or metered application of the topical substance. Increasing the number of times that the trigger 107 is pressed increases the amount of substance released through the applicator head 120. Likewise, increasing the cable action and increases the amount of substance released through the applicator. A metered dose can be determined based upon these geometries. Further, the trigger 107 may have a locking mechanism to prevent accidental activation of the trigger, and unwanted loss of the topical substance. Further, the handle 110 may include a display on the Arm 1 (207), e.g., LED display, for showing the amount of topical substance that is being dispensed by the applicator device 100.

Figure 6B:
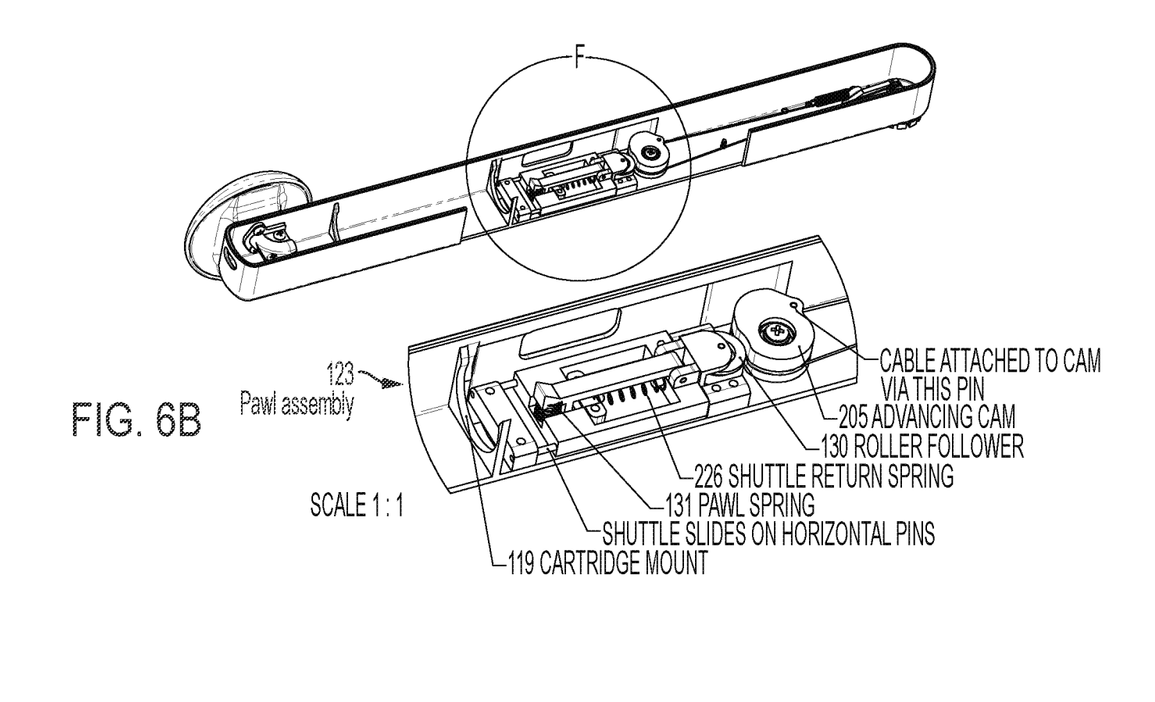
FIG. 6B shows a perspective and detailed-view of the internal mechanisms of an example applicator device including a shuttle, locking joint, and syringe cartridge mount that provides for metered dosing.

As shown in FIGS. 4A-6B, the applicator device 100 includes internal actuation components that mechanically deliver the topical substance to the patient. As the trigger 107 is depressed, the cable 108 passes through the rotating (articulated) joint 200 via two pulleys 115 that position the cable 108 coaxially with the joint (as shown in FIGS. 4A-5C). Pressing the trigger 107 actuates the "shuttle" slider assembly 109, which functions by moving along the horizontal pins 119 as seen in FIGS. 6A-6C. The motion of the slider shuttle assembly 109 provides advancement of the cable 108 via the advancing cam 205, which pushes the roller follower 130 upward, which causes the pawl assembly 123 to rotate about the pawl axis spring 131. This motion results in longitudinal motion of the ratcheting pawl 133 in the opposite direction of pull cable 108, which engages with the teeth 606 on the syringe plunger 112 and ultimately pushes the syringe plunger 112 to move the topical substance through the syringe (cartridge) 105 and out of syringe tip 114. Syringe tip 114 attaches to the applicator head 120 via a cavity 206 in Arm 2 (208) shown in FIGS. 3A-3C. In other embodiments, the trigger 107 initiates an electronically powered switch to activate the pawl assembly 123 to rotate about the pawl axis spring 131. In other embodiments, the applicator head 120 includes a flow directing tubing to seal with the syringe body to allow the topical substance to flow from a syringe opening (without a syringe tip, thus making seating of the syringe simpler) to the applicator head 120 via the flow directing tubing.

Returning to FIGS. 4A-6B, when the trigger 107 is released, the cable return spring 116 (and shuttle return spring 226) causes the shuttle slider 109 to return to its resting position, and the pawl assembly 123 rotates back to its resting position, and the cable return spring 116 between the roller follower arm 130 and the pawl assembly 123 allows sufficient freedom of motion for the tooth 133 on the pawl spring 131 to skip to the next tooth on syringe plunger 112, preparing the mechanism and device for a subsequent dose delivery upon the next pressing of the trigger 107.

Figure 2A:
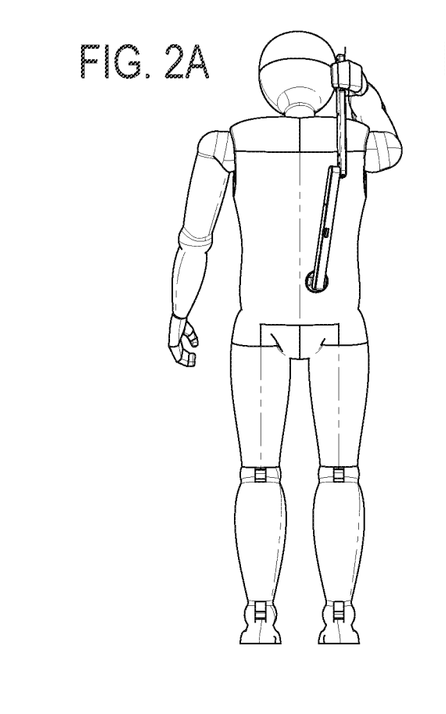
FIGS. 2A-2C show an example applicator device of the invention from various angles and in use by a person to apply a topical substance and demonstrates a fully-extended configuration of the applicator device.
Figure 2B:
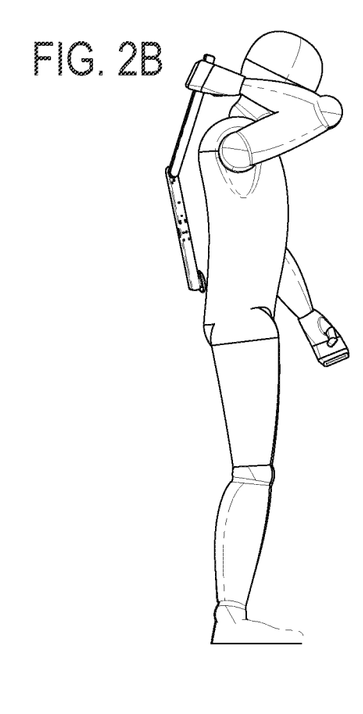
Figure 2C:
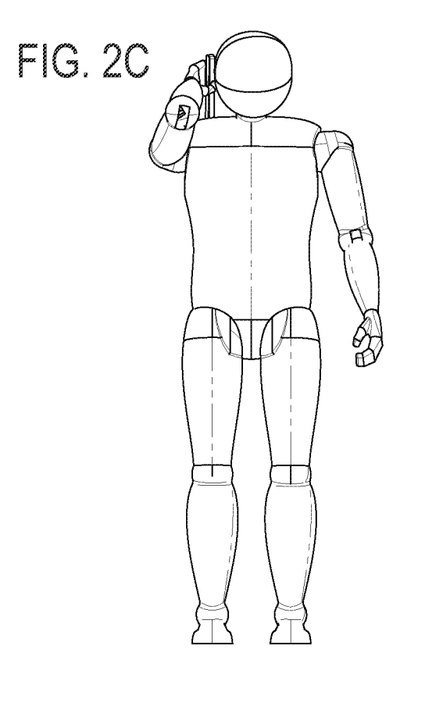
Figures 3A, 3B, 3C:
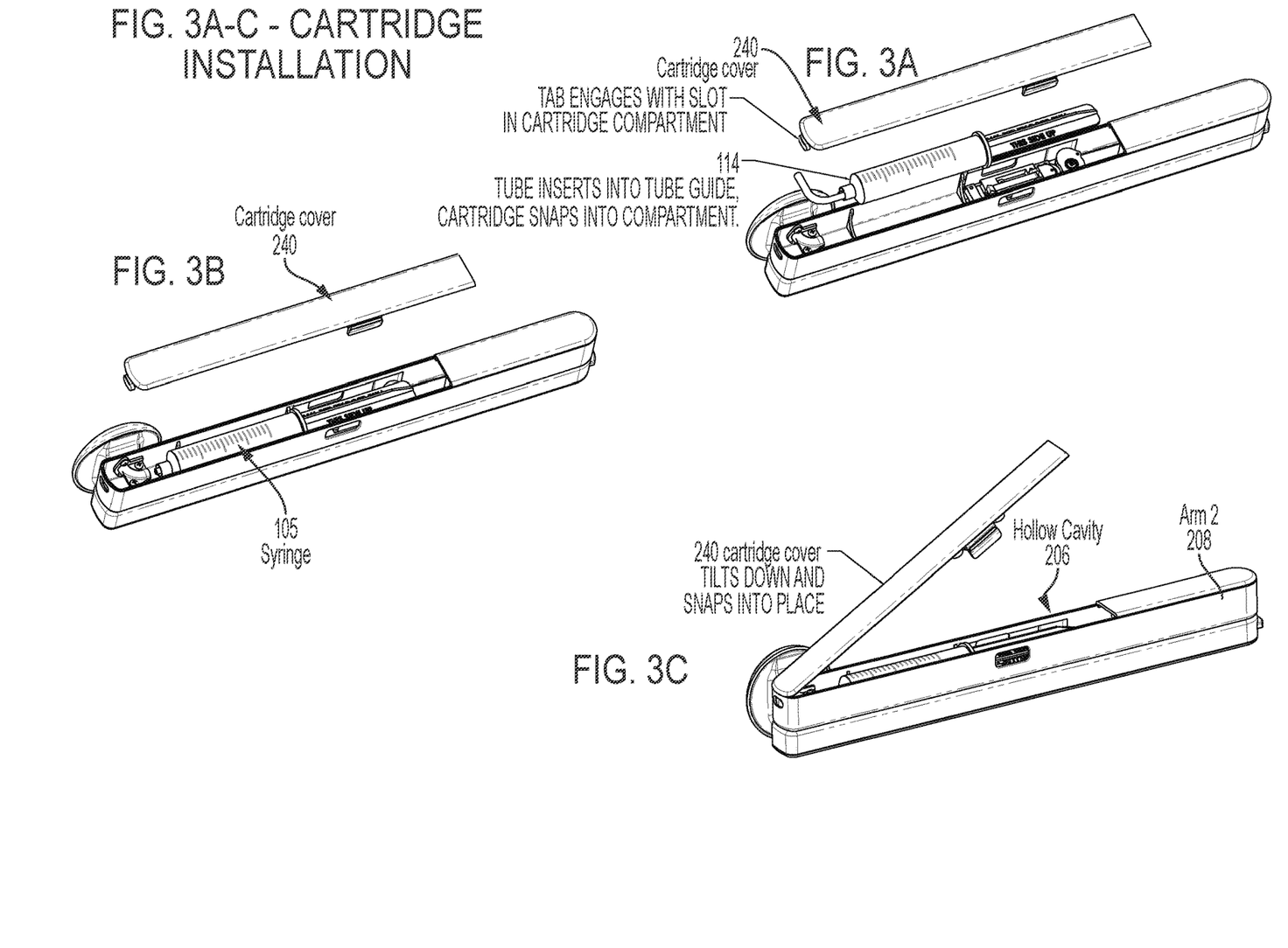
FIG. 3A shows a perspective-view of an arm of an example applicator device with a cover removed to place a syringe cartridge that is also separated from the applicator device.
FIG. 3B shows a perspective-view of an arm of an example applicator device with a cover removed with a syringe cartridge placed inside the applicator device.
FIG. 3C shows a perspective-view of an arm of an example applicator device with a cover in an intermediate closing state with a syringe cartridge placed inside the applicator device.
Figure 8:
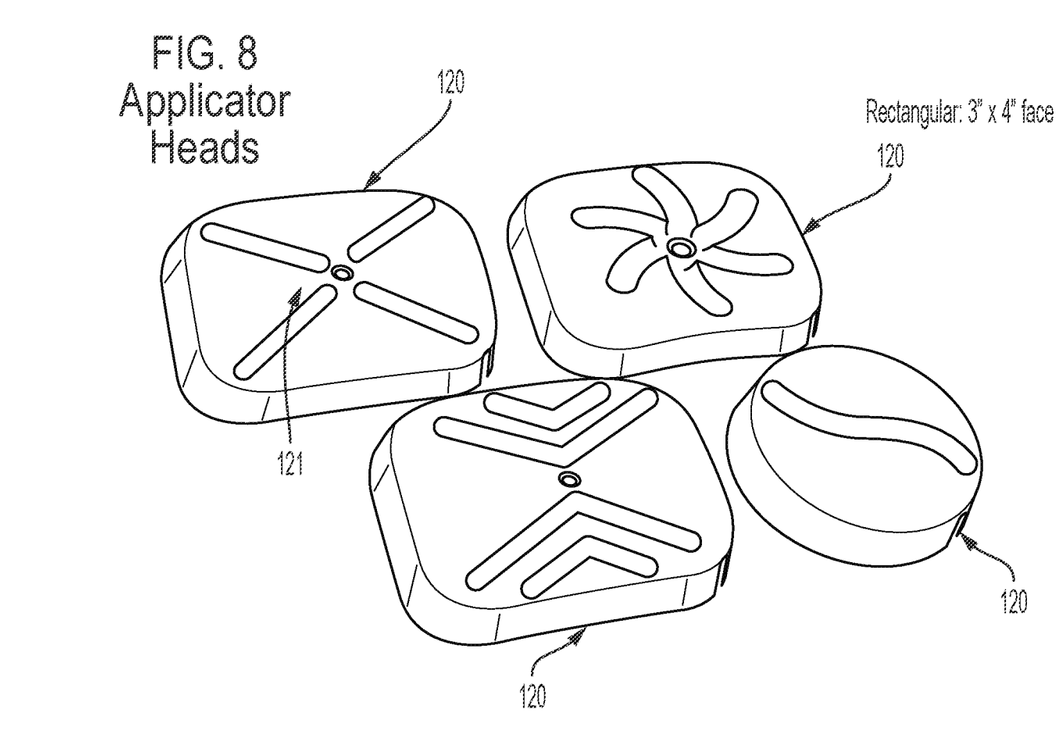
FIG. 8 shows a perspective-view of example applicator heads of the invention.

As the cable 108 moves the predetermined length during each trigger activation, the force of the cable 108 moves a corresponding specific amount of medicine (or other substance) through the syringe (cartridge) 105 in the cavity 206 through the incorporation portion 204 to the applicator head 120. In the examples, a metered dose of 1 ml is delivered with each pull of the trigger 107, which is achieved via specific tooth spacing on syringe plunger 112, such that the amount of topical substance dispensed is equal to the syringe's internal cross-sectional area times the spacing between teeth on the plunger 112. The amount of topical substance released is controlled by the number of times the trigger 107 is pulled. Each activation of the trigger 107 equates to the release of a specific amount or metered application of the topical substance through the syringe tip 114 and out through the applicator head 120 and then through the opening 121 in the applicator head 120 as shown in FIGS. 2, 4, and 8, for example.

The cavity 206 can hold and store the topical substance (e.g., liquid, cream, ointment, gel, and other substances) using a syringe 105 or other cartridge configuration where a cartridge or vial, or other substance container is placed into the hollow cavity 206 of incorporation portion 204, and the cable 108 acts upon the syringe, cartridge, substance container, or vial to move the substance a predetermined amount (distance). The substance container may include syringes, cartridges, vials, attachable bellows, plastic bottles, or other containers which may be different sizes and filled with the topical substances. A syringe may store a set volume between a 20 and 90 g or ml of a topical substance. The substance containers may be pre-filled (e.g., by a manufacturer) for attachment and immediate use by the device. The substance containers may include an easy attachment mechanism that mates with corresponding parts of the cavity 206. The substance containers may include durable materials such as plastic and stainless steel, and be easy to wash, clean, and/or disinfect, e.g., be dishwasher safe.

The cavity 206 may be adjustable in size or be sized to contain specific volume containers. For example, a smaller syringe with a 30 ml volume may be used in a cavity 206 sized for only a 30 ml syringe, and a larger syringe with a 60 ml volume may be used in a cavity 206 sized for a 60 ml syringe. The syringe 105, cartridge, substance container, or vial may be pre-loaded with the topical substance. The cavity 206 can also be modified to be detached to receive a (topical) substance and then reattached to the applicator device 100. For example, an anti-itch cream can be inserted in a pre-filled syringe 105 or cartridge in cavity 206, and the cavity 206 can be reattached to the applicator device 100 on Arm 2 (208). Cover 240 secures the cavity 206 safeguarding syringe 105 for use and can also provide a seal between right-angle syringe tip 114 and the back of the applicator head 120 as shown in FIGS. 3, 4, 6, and 7. The cavity 206, syringe 105, and applicator head 120 are configured to be cleaned by flushing with a liquid, e.g., saline.

Returning to FIGS. 1 and 5, upon activating the trigger 107, once the topical substance flows from syringe 105, the substance flows through applicator head 120. As shown in FIG. 8, applicator head 120 can be substantially round, as shown, or can be other geometric shapes and sizes, depending upon patient size and mobility, the substance to be applied to the patient's affected area, and the patient's diagnosis. In any case, applicator head 120 includes an internal passage 555 (shown in FIGS. 4C, 5C, and 7) that allows the substance to flow into the applicator head 120 and through opening 121 or other orifice through which the applicator head 120 delivers the substance to the affected area of the patient.

The applicator head 120, as well as the other components of the device in fluid communication, can be attached and connected using O-rings to seal the junctions. In the FIGS., a single circular orifice (opening 121) is shown in the center of the round applicator head 120 where the topical substance will be dispensed, but other geometries and numbers of openings 121 can also be used in the applicator head 120, depending upon patient size and mobility, the substance to be applied to the patient's affected area, and the patient's diagnosis. For example, in some embodiments, multiple openings may be in the applicator head 120 to spread delivery of the topical substance throughout the applicator head 120. In one embodiment, the applicator head 120 may include a rolling ball applicator. The applicator head 120 may be made of durable materials such as plastic and stainless steel. The applicator head 120 may include a cover or pads that may be slipped-on or attached to the applicator head 120. The cover or pads may be changed to keep the applicator head 120 sanitary. The applicator head 120 may include a kneading or massage mechanism configured to shake or pound the applicator head 120 against the patient during use. The applicator head 120 may be easily detachable. The applicator head may be detachable to provide an opening to fill cavity 206 with the topical substance. The applicator head 120 may include another elbow joint to rotate and lock the applicator head 120 in a convenient position during use. Again, the applicator head 120 elbow joint may be similar to the rotating joint 200. The applicator head 120 may include a mirror or other visual aid, e.g., a video application, that allows for viewing of the patient while being the topical substance is applied.

The applicator head 120 may be various shapes, e.g., round, square, triangular, oval, etc., and sizes, e.g., round diameters between 1.5 and four inches or squares of two by two inches. Regardless of the size and configuration of the applicator head 120, it is placed in contact with the patient's skin, and the topical substance reaches the end of the device 100 and is then applied to the hard to reach area of the body. The medicine is massaged into the desired area using the applicator head 120 of the device 100 while the user holds the handle 110 of the device 100 at the opposite end. Between applications or between uses, the device can be easily cleaned and disinfected.

The claimed invention is:

1. An applicator device for self-administration of a topical substance to a difficult-to-reach location of a patient, the applicator device comprising:
    a handle with a proximal end extending along a first arm to a distal end, an actuation path of the handle extending from the proximal end to the distal end, and a rotating joint at the distal end;
    an articulating segment including:
        a joint end extending along a second arm to an applicator end, and
        an incorporation portion of the second arm between the joint end and the applicator end, the incorporation portion configured to accept the topical substance to be administered to the patient, wherein the articulating segment is operably connected to the handle via the rotating joint at the joint end;
            wherein the incorporation portion accepts a syringe holding the topical substance to be administered to the patient, and
    an applicator head for administering the topical substance to the patient, the applicator head in fluid communication with the incorporation portion to administer the topical substance to the patient; and
    an actuator positioned in the handle and configured to initiate administration of the topical substance to the patient when activated, wherein the actuator includes a cable extending from the handle through the rotating joint to a slider in the articulating segment, and
        wherein the actuator activates the cable and displaces the cable a pre-determined distance each time it is activated to mobilize a syringe plunger that propels the topical substance from the syringe through the incorporation portion along a flow path to an orifice in the applicator head, to administer a metered dose of the topical substance to the patient; and
        wherein activating the actuator moves a shuttle slider assembly that moves along pins and advances the cable via an advancing cam, the advancing cam pushes a roller follower upward to cause a pawl assembly to rotate about a pawl axis spring resulting in longitudinal motion of a ratcheting pawl in the opposite direction of the cable, the ratcheting pawl engages teeth on the syringe plunger to mobilize the syringe plunger to force the topical substance to the orifice in the actuator head to administer the metered dose of the topical substance to the patient.

2. The applicator device of claim 1, wherein the metered dose is determined by at least one of a number of activations of the actuator, tooth spacing on the syringe plunger, and internal cross-sectional area of the syringe.

3. The applicator device of claim 1, wherein the rotating joint includes two pulleys through which the cable extends coaxially through the rotating joint from the handle to the articulating member.

4. The applicator device of claim 1, wherein the rotating joint includes a joint unlocking button configured to hold the handle and the articulating segment in a predetermined closed position relative to each other and to position the handle and the articulating segment in an extended configuration when engaged.

5. The applicator device of claim 4, wherein the joint unlocking button includes a joint locking wheel with a notch to engage the rotating joint to hold the handle and the articulating segment in a predetermined extended configuration when engaged.

6. The applicator device of claim 1, wherein at least one of the handle and the articulating segment are extendible to elongate the applicator device to up to an additional eight (8) inches in overall length, as measured from the proximal end of the handle to the applicator head on the articulating segment.

7. An applicator device for self-administration of a topical substance to a difficult-to-reach location of a patient, the applicator device comprising:
- a handle with a proximal end extending along a first arm to a distal end, an actuation path of the handle extending from the proximal end to the distal end, and a rotating joint at the distal end;
- an articulating segment including:
  - a joint end extending along a second arm to an applicator end, and
  - an incorporation portion of the second arm between the joint end and the applicator end, the incorporation portion configured to accept a cartridge holding the topical substance to be administered to the patient, wherein the articulating segment is operably connected to the handle via the rotating joint at the joint end;
- an applicator head for administering the topical substance to the patient, the applicator head in fluid communication with the cartridge to administer the topical substance to the patient; and
- the cartridge containing the topical substance to be administered to the patient, and wherein an actuator propels the topical substance from the cartridge through the incorporation portion along a flow path to an orifice in the applicator head to administer a metered dose of the topical substance to the patient; and
- wherein the actuator includes a cable extending from the handle through the rotating joint to a slider in the articulating segment, and wherein the actuator activates the cable and displaces the cable a pre-determined distance each time it is activated to mobilize a driver of the cartridge that propels the topical substance through the incorporation portion along a flow path to the orifice in the applicator head, to administer the metered dose of the topical substance to the patient; and
- wherein activating the actuator moves a shuttle slider assembly that moves along pins and advances the cable via an advancing cam, the advancing cam pushes a roller follower upward to cause a pawl assembly to rotate about a pawl axis spring resulting in longitudinal motion of a ratcheting pawl in the opposite direction of the cable, the ratcheting pawl engages teeth on the driver to mobilize the driver to force the topical substance to the orifice in the actuator head to administer the metered dose of the topical substance to the patient.

8. The applicator device of claim 7, wherein the metered dose is determined by at least one of a number of activations of the actuator, tooth spacing on the syringe plunger, and internal cross-sectional area of the syringe.

* * * * *